United States Patent [19]

Favier et al.

[11] 4,400,381
[45] Aug. 23, 1983

[54] PIPERAZINE DERIVATIVES OF THEOPHYLLINE

[75] Inventors: Colette Favier, Neuilly-sur-Seine; Henri Pinhas, Paris; Serge Beranger, Bretigny-sur-Orge; Jean-Claude Pascal, Cachan, all of France

[73] Assignee: Laroche-Navarron, S.A., Puteaux, France

[21] Appl. No.: 288,836

[22] Filed: Jul. 31, 1981

[51] Int. Cl.³ .................... A61K 31/52; C07D 473/08
[52] U.S. Cl. ........................ 424/248.52; 424/248.55; 424/248.58; 424/253; 544/118; 544/271; 544/272
[58] Field of Search .................. 424/253, 250, 248.52, 424/248.55, 248.58; 544/271, 272, 118

[56] References Cited

U.S. PATENT DOCUMENTS

| | | | |
|---|---|---|---|
| 2,924,598 | 2/1960 | Heinrich et al. | 544/118 |
| 3,030,363 | 4/1962 | Konz et al. | 544/272 |
| 3,642,798 | 2/1972 | Nitta et al. | 544/270 |
| 3,734,911 | 5/1973 | Bestian | 424/253 |
| 3,896,119 | 7/1975 | Klingler | 544/118 |

Primary Examiner—Paul M. Coughlan, Jr.
Attorney, Agent, or Firm—Tom M. Moran; Alan M. Krubiner

[57] ABSTRACT

New compounds of the formula

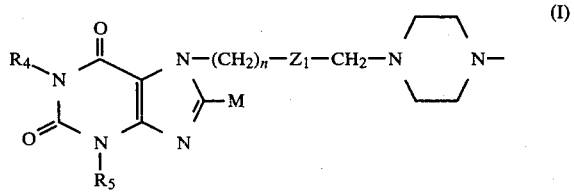

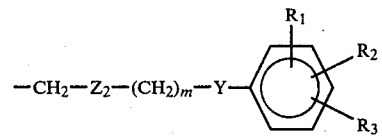

and the pharmaceutically acceptable acid addition salts thereof, wherein M is selected from the group consisting of hydrogen, morpholino, benzylamino, di-n-lower alkylamine, n-lower alkylamine, and aryl piperazino;

$Z_1$ and $Z_2$ are each independently selected from the group consisting of $CH_2$, CHOB and C=O, wherein B is selected from the group consisting of hydrogen and alkanoyl;

Y is oxygen or sulfur;

n is an integer from 0–4 but cannot be zero when $Z_1$ is CHOB;

m is an integer from 0–4 but cannot be zero when $Z_2$ is CHOB, or when m is hydrogen;

$R_1$, $R_2$ and $R_3$ are each independently hydrogen, halogen, hydroxy, trifluoromethyl, alkyl or alkoxy; and $R_4$ and $R_5$ are each independently lower alkyl, with the proviso that both $R_4$ and $R_5$ cannot be methyl when M is hydrogen;

are antihistamines and are therefore useful in the treatment of respiratory diseases including asthma, hay fever, allergies and the common cold. They are also vasodilators.

17 Claims, No Drawings

PIPERAZINE DERIVATIVES OF THEOPHYLLINE

BACKGROUND OF THE INVENTION

This invention relates to piperazine derivatives of theophylline; to their utility as treatment compounds for respiratory and allergic diseases, and to their properties as vasodilators.

Theophylline, itself, is well known as a diuretic, cardiac stimulant and smooth muscle relaxant. Addition of the piperazine containing substituent confers a range of pharmacologic activities which render the resulting compounds useful in the symptomatic treatment of asthma, hay fever and other respiratory diseases such as, for example, the common cold. Those compounds of others most similar in structure to the compounds of the present invention are those in European patent application No. 23,350. Also, similar compounds have been described by us in U.S. application Ser. No. 224,710, filed Jan. 12, 1981, U.S. Pat. No. 4,374,835. The compounds of the present invention are also vasodilators.

SUMMARY OF THE INVENTION

The present invention concerns novel compounds of the formula

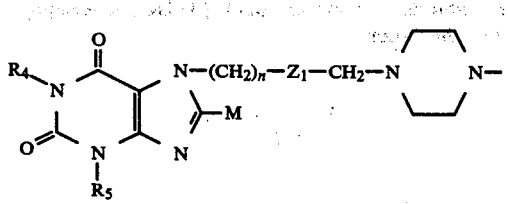
(I)

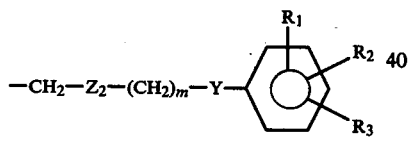

and the pharmaceutically acceptable acid addition salts thereof, wherein

M is selected from the group consisting of hydrogen, morpholino, benzylamino, di-n-lower alkylamine, n-lower alkyllamine, and

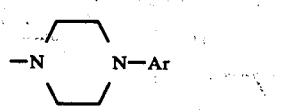

wherein Ar is optionally substituted phenyl;

$Z_1$ and $Z_2$ are each independently selected from the group consisting of $CH_2$, CHOB and C=O, wherein B is selected from the group consisting of hydrogen and alkanoyl;

Y is oxygen or sulfur;

n is an integer from 0–4 but cannot be zero when $Z_1$ is CHOB;

M is an integer from 0–4 but cannot be zero when $Z_2$ is CHOB, or when m is hydrogen;

$R_1$, $R_2$ and $R_3$ are each independently hydrogen, halogen, hydroxy, trifluoromethyl, alkyl or alkoxy; and $R_4$ and $R_5$ are each independently lower alkyl, with the proviso that both $R_4$ and $R_5$ cannot be methyl when M is hydrogen.

In another aspect, this invention concerns pharmaceutical compositions containing the above compounds as active ingredients.

In other aspects, the invention concerns methods for treating, or relieving the symptoms of, respiratory disorders and of effecting vasodilation using the above compounds, (or pharmaceutical compositions containing them); and such compositions.

In a final aspect, the invention concerns processes for preparing these compounds.

DETAILED DESCRIPTION OF THE INVENTION

Definitions

As used herein:

"n-Lower alkyl" means an unbranched saturated hydrocarbon chain of 1–4 carbons: methyl, ethyl, n-propyl, n-butyl.

"Lower alkyl" means a branched or unbranched saturated hydrocarbon chain of 1–4 carbons, such as, for example, methyl, ethyl, n-propyl, i-butyl and the like "Lower alkoxy" means —OR wherein R is lower alkyl as defined.

"Alkyl" means a branched or unbranched saturated hydrocarbon chain containing 1-6 carbon atoms, such as methyl, ethyl, propyl, tert-butyl, n-hexyl and the like;

"Alkoxy" means —OR wherein R is alkyl as herein defined.

"Alkanoyl" means

wherein R is alkyl as defined herein.

"Halogen" means chloro, bromo or iodo.

"Pharmaceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, menthanesulfonic acid, ethanesulfonic acid, p-toluenesulfonic acid, salicylic acid and the like.

"Aryl piperazino" is a group with the structural formula:

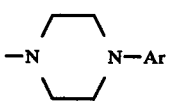

which is attached to the imidazole ring of theophylline at position 7, and wherein Ar is optionally substituted phenyl.

"Optional" or "optionally" means that the subsequently described event of circumstance may or may not occur, and that the description includes instances where said event or circumstance occurs and instances in which it does not. For example, "optionally substituted phenyl" means that the phenyl may or may not be substituted and that the description includes both unsubstituted phenyl and phenyl wherein there is substitution; "optionally followed by converting the free base to the acid addition salt" means that said conversion may or may not be carried out in order for the process described to fall within the invention, and the invention includes those processes wherein the free base is converted to the acid addition salt and those processes in which it is not.

"Substituted phenyl" as used herein means that one or more hydrogens of the phenyl ring are replaced by moieties selected from the group consisting of lower alkyl, lower alkoxy, halo and trifluoromethyl. In the context of the present invention, said replacement may be at any position of the phenyl ring, and a maximum of 3 hydrogens may be so replaced.

In the reaction schemes as shown herein, and in the claims:

"The" represents the appropriate theophylline moiety wherein linkage will be formed at the imidazole nitrogen as indicated:

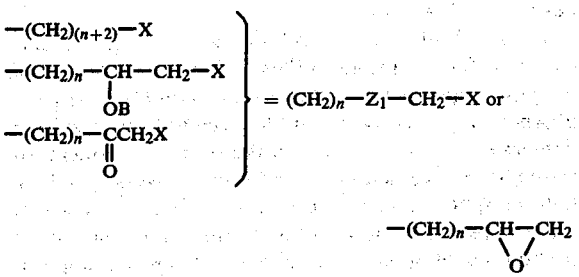

which will sometimes herein be called 8-M-1-$R_4$-3-$R_5$,7-dihydro-1H-purine-2,6-dion-7-yl.

"X" represents a halogen atom; i.e. chloro, bromo or iodo; however, each X shown may be selected independently from this group;

"A" represents a moiety selected from the group consisting of

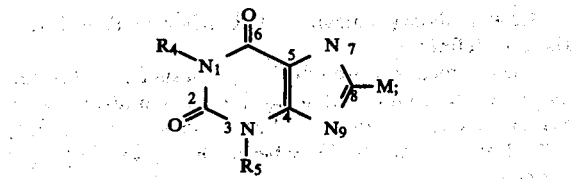

wherein n is as herein defined.

Process for Preparation

Reaction Schemes 1 and 2, shown below, are complementary processes for linking the two "halves" of the compounds of Formula I through the piperazine ring, by reacting the theophylline containing segment with the phenyl containing segment in processes wherein the piperazine attached to one segment displaces a leaving group from the other.

REACTION SCHEME 1

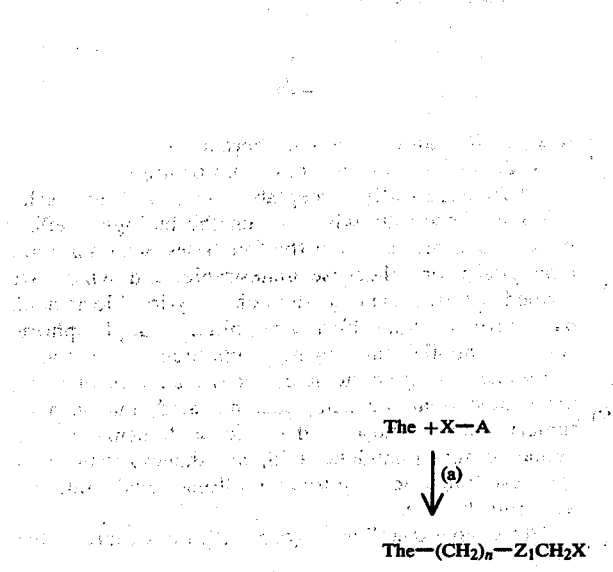

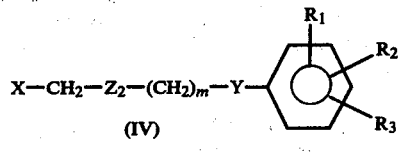

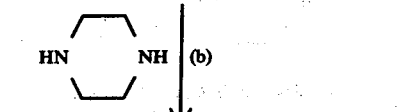

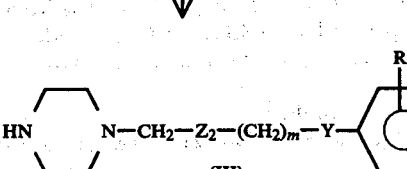

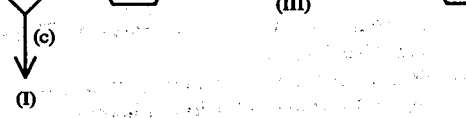

REACTION SCHEME 2

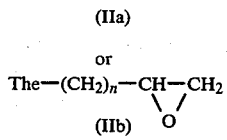

(IIa)

or

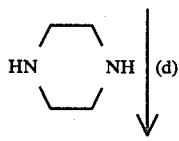

(IIb)

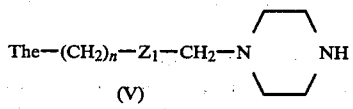

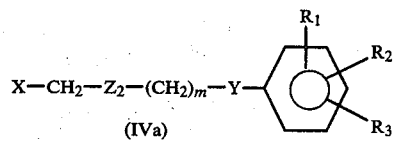

(IVa)

or

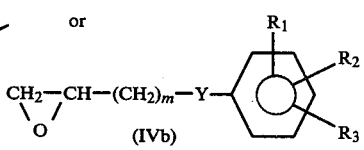

(IVb)

(I)

In the reaction schemes shown, isolation and purification of the compounds and intermediates described, whether in the body of the specification, or examples, can be effected, if desired, by any suitable separation or purification procedure such as, for example, filtration, extraction, crystallization, column chromatography, thin-layer chromatography or thick-layer chromatography, or a combination of these procedures. Specific illustrations of suitable separation and isolation procedures can be had by reference to the examples hereinbelow. However, other equivalent separation or isolation procedures could, of course, also be used.

The salt products are also isolated by conventional means. For example, the reaction mixtures may be evaporated to a dryness, and the salts can be further purified by conventional methods.

The compounds of the present invention in which $Z_1$ and/or $Z_2$ is CHOB and, which therefore, contain at least one chiral center, may be prepared in either optically active form or as racemic mixtures. Unless otherwise specified, the compounds described herein are all in the racemic form. However, the scope of the subject invention herein is not to be considered limited to the racemic forms, but to encompass the individual optical isomers of the compounds.

If desired, the compounds herein may be resolved into their optical antipodes by conventional resolution means; for example by separation (e.g. fractional crystallization) of the diastereomeric salts formed by the reaction of these compounds with optically active acids. Exemplary of such optically active acids are the optically active forms of camphor-10-sulfonic acid, 2-bromo-camphor-sulfonic acid, camphoric acid, menthoxyacetic acid, tartaric acid, malic acid, diacetyltartaric acid, pyrrolidine-5-carboxylic acid and the like. The separated pure diastereomeric salts may then be cleaved by standard means to afford the respective optical isomers of the compounds of Formula (I).

In those embodiments wherein both $Z_1$ and $Z_2$ are —CHOB, the compound contains two chiral centers, and hence 4 stereoisomeric forms—two diastereomeric pairs of enantiomers—exist. The invention herein includes mixtures of any or all of these stereoisomeric forms and said pure stereoisomeric forms. Enantiomers may, if desired, be separated as outlined above. Diastereomers may, of course, be separated by standard means used to separate chemical compounds in general, as are well known by those skilled in the art.

Alkylated analogs of theophylline, which are included in the designation "The" are prepared as described in *J. Am. Chem. Soc.*, 75:114(1953). Substitution with an amine at position 8 is carried out by means known in the art, by first brominating the 8-position, followed by reaction with a suitable amine. The theophylline or its alkylated analog is dissolved in acidic aqueous medium at about 10°–80° C., preferably about 45°–55° C. and bromine is added dropwise in slight molar excess. The brominated product is then refluxed with the appropriate amine for about 1–8 hours, preferably about 1–3 hours.

Reaction Schemes 1 and 2 have, in common, step (a), the condensation of the theophylline moiety with a halide containing the desired side chain. The reaction is carried out in the presence of a polar solvent, such as for example, aqueous alkanol, a pure polar alcohol, polar ketone, or water, preferably aqueous isopropanol, and using a basic catalyst such as, e.g. sodium or potassium hydroxide or carbonate, preferably potassium hydroxide. The reaction is carried out at elevated temperatures of about 70°-120°, most conveniently at the reflux temperature of the solvent. An equimolar amount to several-fold molar excess, preferably about 1 mole to 2 moles of X-A per mole of the theophylline.

Compounds of Formula IV (IVa and IVb) are described in European patent application No. 79/400.214.7. They are prepared in a manner similar to that described in step (a) for the preparation of compounds of Formula IIa and IIb, but substituting the appropriate phenol or thiophenol for the theophylline moiety. As described above, the reaction is carried out in a polar solvent at elevated temperatures with a basic catalyst and, similarly, using either equimolar amounts or a molar excess of the compound of formula X-A over the substrate phenol or thiophenol.

The condensations of the compounds of Formula IV with piperazine to yield compounds of Formula III (step b, reaction scheme 1) and of compounds of Formula II with piperazine to yield compounds of Formula V (step d, reaction scheme 2) are carried out in similar fashion. In each case, an excess of piperazine (about 1.5-4 fold, preferably 2-3 fold molar excess) is heated to reflux with the halide in the presence of a polar solvent such as methyl ethyl ketone (MEK), water, ethanol and the like, preferably alcohol-water. Reaction is continued for about 12-36 hours, preferably 20-25 hours. A basic catalyst, as described above for step (a) is used, in this case, preferably, sodium hydroxide. The resulting piperazine adduct is then isolated by conventional means, known to those skilled in the art.

The condensations represented by steps (c) of scheme 1, and step (e) of scheme 2 are again similar, both to each other and to the steps previously described. The reaction conditions approximate those described above as to solvent, catalyst, time and temperature. However, approximately equimolar amounts of the reactants containing the two ends of the molecule are employed.

The reaction schemes as shown offer methods to prepare all of the compounds of the present invention. However, it should be noted, in addition, that compounds of Formula I wherein $Z_1$ and/or $Z_2$ is C=O may be reduced to the corresponding alcohols of Formula I using a metal hydride, such as, for example, $KBH_4$ or $NaBH_4$ in a polar solvent, such as aqueous methanol. The reduction is accomplished by dissolving the substrate carbonyl in the solvent chosen, and adding an excess (the amount of excess depending on the side reaction with solvent) of the hydride in small portions with stirring until reaction is complete. The temperature is kept at about 0°-25° C., preferably 4°-15° C.

Conversely, compounds of Formula I wherein $Z_1$ and/or $Z_2$ is CHOH may be oxidized to the corresponding carbonyls under suitable, mild conditions. Appropriate oxidizing agents include, for example, dilute neutral permanganate or chromic acid, preferably permanganate. The substrate alcohol is dissolved in a polar solvent such as alcohol, MEK, or alkanol-water, and a solution of the oxidizing agent added until reaction is complete. Approximately stoichiometric amounts of oxidizing agent are required. The temperature is kept at about 5°-30° preferably 15°-20° C.

Also, compounds of Formula I wherein $Z_1$ and/or $Z_2$ is CHOH may be esterified to convert them to the alkanoyl derivatives. This is accomplished by heating the compound of Formula I with a molar excess of the appropriate carboxylic anhydride or chloride in a tertiary amine solvent, such as, for example, pyridine. The temperature is kept at about 20°-90°, preferably 15°-30°.

Conversely, the compounds of Formula I wherein $Z_1$ and/or $Z_2$ is

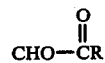

may be hydrolyzed, using conventiona methods, well known to those in the art to the corresponding alcohols: The ester is heated in a water solution with an acid or basic catalyst until hydrolysis is complete.

Salts of the compounds of Formula I are prepared by reacting the corresponding free bases with appropriate acids or acid salts at a temperature of between 0° and 100° C. Conversely, free bases can be prepared by reacting corresponding acid addition salts with suitable alkaline agents, such as sodium or potassium hydroxide at 0°-100° C.

The products of Formula I or the salts thereof, synthesized by any of the pathways disclosed herein are optionally converted, when appropriate, to either the free base, or to any salt, said salts including, but not being limited to the pharmaceutically acceptable acid addition salts.

Preferred Embodiments

Preferred embodiments of the compounds of this invention are those wherein n and m are both 1; $Z_1$, and $Z_2$ are CHOH or $CH_2$; and at least one of $R_1$, $R_2$ and $R_3$ is hydrogen, and the pharmaceutically acceptable acid addition salts thereof.

Especially preferred among these are compounds and their salts wherein:

either at least one of $R_4$ and $R_5$ is methyl, or both $R_4$ and $R_5$ are identical; and either at least two of $R_1$, $R_2$ and $R_3$ are hydrogen or two of these are otherwise identical.

Especially referred among this latter group are compounds and their salts selected from the group consisting of 1-[3-(3-i-butyl-1-methyl-3,7-dihydro-1H-purine-2,6-dion-7-yl)-2-hydroxypropyl]-4-(3-phenylthiopropyl)-piperazine;

1-[3-(8-morpholino-3-i-butyl-1-methyl-3,7-dihydro-1H-purine-2,6-dion-7-yl)-2-hydroxypropyl]-4-(3-phenylthiopropyl)piperazine;

1-[3-(3-i-butyl-1-methyl-3,7-dihydro-1H-purine-2,6-dion-7-yl)-2-hydroxypropyl]-4-(3-phenoxypropyl)-piperazine;

1-[3-(3-i-butyl-1-methyl-3,7-dihydro-1H-purine-2,6-dion-7-yl)-2-hydroxypropyl]-4-(3-phenylthio-2-hydroxypropyl)-piperazine;

1-[3-(3-i-butyl-1-methyl-3,7-dihydro-1H-purine-2,6-dion-7-yl)-2-hydroxypropyl]-4-[3-(4-methylphenylthio)propyl]-piperazine;

1-[3-(3-n-butyl-1-methyl-3,7-dihydro-1H-purine-2,6-dion-7-yl)-2-hydroxypropyl]-4-(3-phenylthiopropyl)-piperazine;

1-[3-(3-i-butyl-1-methyl-3,7-dihydro-1H-purine-2,6-dion-7-yl)propyl]-4-(3-phenoxypropyl)-piperazine;

1-[3-(8-morpholino-1,3-dimethyl-3,7-dihydro-1H-purine-2,6-dion-7-yl)-2-hydroxypropyl]-4-(3-phenylthiopropyl)piperazine;

1-[3-(8-morpholino-1,3-dimethyl-3,7-dihydro-1H-purine-2,6-dion-7-yl)-2-hydroxypropyl]-4-[3-(4-methylphenyl)thiopropyl]piperazine;

1-[3-(8-n-butylamino-1,3-dimethyl-3,7-dihydro-1H-purine-2,6-dion-7-yl)-2-hydroxypropyl]-4-[3-(2,6-dimethylphenoxy)-propyl]piperazine;

1-[3-(8-morpholino-3-n-butyl-1-methy-3,7-dihydro-1H-purine-2,6-dion-7-yl)-2-hydroxypropyl]-4-(3-phenylthiopropyl)piperazine.

Utility and Administration

The compounds of the present invention are particularly effective antihistamines in mammals. They have been demonstrated to antagonize the effects of histamine in a variety of tests related to such activity, including their activity in prevention of anaphylactic shock in rats, bronchodilation in guinea pigs, inhibition of muscle contraction in response to stress in rats, and brachycardial effects in guinea pigs. Therefore, the compounds are useful in the treatment of respiratory diseases and allergic reactions in mammals, including, but not limited to, asthma, hay fever, and the common cold. They have also been shown to be vasodilators in humans.

For use as antihistamines, administration of the active compounds and salts described herein can be via any of the accepted modes of administration for antihistaminic agents which relieve congestion or otherwise effect the control of allergic or other respiratory symptoms. These methods include oral, parenteral and otherwise systemic, or aerosol forms. Preferred dosage forms are oral or aerosol compositions. Depending on the intended mode, the compositions may be in the form of solid, semi-solid or liquid dosage forms, such as, for exampole, tablets, suppositories, pills, capsules, powders, liquids, suspensions, or the like, preferably in unit dosage forms suitable for single administration of precise dosages. The compositions will include a conventional pharmaceutical carrier or excipient and an active compound of Formula I or the pharmaceutically acceptable salts thereof and, in addition, may include other medicinal agents, pharmaceutical agents, carriers, adjuvants, etc.

The amount of active compound administered will of course, be dependent on the subject being treated, the severity of the affliction, the manner of administration and the judgment of the prescribing physician. However, an effective dosage is in the range of 0.1–500 μg/kg/day, preferably 5–100 μg/kg/day. For an average 70 kg human, this would amount to 7 μg to 35 mg per day, or preferably 35 μg to 7 mg/day.

Typical compositions contain 0.01–95% by weight of active ingredient, with the balance one or more acceptable non-toxic carriers. The percentage of active ingredient, will, of course, depend upon the dosage form and the mode of administration.

For solid compositions, conventional non-toxic solid carriers include, for example, pharmaceutical grades of mannitol, lactose, starch, magnesium stearate, sodium saccharin, talcum, cellulose, glucose, sucrose, magnesium carbonate, and the like may be used. The active compound as defined above may be formulated as suppositories using, for exampole, polyalkylene glycols, for example, propylene glycol, as the carrier. Liquid pharmaceutically administerable compositions can, for example, be prepared by dissolving, dispersing, etc. an active compound as defined above and optional pharmaceutical adjuvants in a carrier, such as, for example, water, saline, aqueous dextrose, glycerol, ethanol, and the like, to thereby form a solution or suspension. If desired, the pharmaceutical composition to be administered may also contain minor amounts of nontoxic auxiliary substances such as wetting or emulsifying agents, pH buffering agents and the like, for example, sodium acetate, sorbitan monolaurate, triethanolamine sodium acetate, sorbitan monolaurate, triethanolamine oleate, etc. Actual methods of preparing such dosage forms are known, or will be apparent, to those skilled in this art; for example, see *Remington's Pharmaceutical Sciences, Mack Publishing Company, Easton, Penna.,* 15th Edition, 1975. The composition or formulation to be administered will, in any event, contain a quantity of the active compound(s) in an amount effective to alleviate the symptoms of the subject being treated.

For oral administration, a pharmaceutically acceptable non-toxic composition is formed by the incorporation of any of the normally employed excipients, such as, for example pharmaceutical grades of mannitol, lactose, starch, magnesium stearate, sodium saccharin, talcum, cellulose, glucose, sucrose, magnesium, carbonate, and the like. Such compositions take the form of solutions, suspensions, tablets, pills, capsules, powders, sustained release formulations and the like. Such compositions may contain 0.1%–95% active ingredient, preferably 1–70%.

For aerosol administration, the active ingredient is preferably supplied in finely divided form along with a surfactant and a propellant. Typical percentages of active ingredients are 0.01 to 20% by weight, preferably 0.04 to 1.0%.

Surfactants must, of course, be non-toxic, and preferably soluble in the propellant. Representative of such agents are the esters or partial esters of fatty acids containing from 6 to 22 carbon atoms, such as caproic, octanoic, lauric, palmitic, stearic, linoleic, linolenic, olestearic and oleic acids with an aliphatic polyhydric alcohol or its cyclic anhydride such as, for example, ethylene glycol, glycerol, erythritol, arabitol, mannitol, sorbitol, the hexitol anhydrides derived from sorbitol (the sorbitan esters sold under the trademark "Spans") and the polyoxyethylene and polyoxypropylene derivatives of these esters. Mixed esters, such as mixed or natural glycerides may be employed. The preferred surface-active agents are the oleates or sorbitan, e.g., those sold under the trademarks "Arlacel C" (Sorbitan sesquioleate), "Span 80" (sorbitan monooleate) and "Span 85" (sorbitan trioleate). The surfactant may constitute 0.1–20% by weight of the composition, preferably 0.25–5%.

The balance of the composition is ordinarily propellant. Liquefied propellants are typically gases at ambient conditions, and are condensed under pressure. Among suitable liquefied propellants are the lower alkanes containing up to five carbons, such as butane and propane; and preferably fluorinated or fluorochlorinated alkanes, such as are sold under the trademark "Freon." Mixtures of the above may also be employed.

In producing the aerosol, a container equipped with a suitable valve is filled with the appropriate propellant, containing the finely divided active ingredient and surfactant. The ingredients are thus maintained at an elevated pressure until released by action of the valve.

For use as vasodilators, oral administration is the preferred mode. The oral compositions and excipients contained therein are similar to those described hereinabove. The dosage level is, again, dependent on the specific circumstances which pertain, but would be in the range of 0.0001 to 5 mg/kg per day, preferably 0.01 to 0.5 mg/kg per day, or, for a 70 kg human 0.007 to 350 mg, preferably 0.7 to 35 mg per day.

Preparations and Examples

The following Preparations and Examples are illustrative of the invention, but are not to be construed as limiting it:

PREPARATION A

Preparation of 8-morholinotheophylline
(8-morpholino-1,3-dimethyl-3,7-dihydro-1H-purine-2,6-dione)

A. One mole of theophylline is dissolved in 2.5 liters of acetic acid containing one liter of water, and kept at 50° C., until the theophylline is dissolved and the medium becomes homogeneous. 1.1 mole of bromine is then added, drop by drop, and the bromine derivative, 8-bromotheophylline precipitates in the medium. The solution is then ccoled to room temperature, and the product filtered and washed with water, and then dried to give 70–85% yield of 8-bromo-theophylline.

0.3 moles of the 8-bromo-theophylline, prepared as in the previous paragraph, is refluxed in 1.5 moles of morpholine for two hours. The precipitate obtained is filtered, to give approximately 80% yield of 8-morpholino-theophylline.

B. Similarly, using the procedure of Paragraph A, but substituting for theophylline its alkylated homologs [as prepared according to the procedure described in *J. Am. Chem. Soc.*, 75: 114 (1953)] one obtains, for example, 8-morpholino-3-i-butyl-1-methyl-3,7-dihydro-1H-purine-2,6-dione;
8-morpholino-3-ethyl-1-methyl-3,7-dihydro-1H-purine-2,6-dione; and
8-morpholino-3-methyl-1-n-propyl-3,7-dihydro-1H-purine-2,6-dione.

C. Similarly, using the procedure in paragraph A, above, but substituting for morpholine, for example,
benzylamine;
n-propylamine; and
diethylamine,
one obtains
8-benzylamino-theophylline;
8-n-propylamino-theophylline;
8-diethylamino-theophylline.

PREPARATION B

Preparation of
3-(8-morpholino-theophyllin-7-yl)-1-chloro-2-hydroxy-propane (compound of formula IIb)

A. 0.2 moles of the 8-morpholino-theophylline is dissolved in 600 ml of ethyl alcohol which contains 0.2 moles of sodium hydroxide, by stirring at 50° C. The solvent is then evaporated under vacuum, and the residue dried. The residue is then refluxed with 0.7 liters of epichlorohydrin. Sodium chloride precipitates during the reflux procedure, and the excess epichlorohydrin is evaporated. The residue is then recrystallized from ethanol to give 3-(8-morpholinotheophyllin-7-yl)-1-chloro-2-hydroxy-propane in approximately 50% yield.

B. Similarly, using the procedure of paragraph A, but substituting for 8-mropholino-theophylline the products listed in paragraph B of Preparation A, one obtains:

3-(8-morpholino-3-i-butyl-1-methyl-3,7-dihydro-1H-purine-2,6-dion-7-yl)-1-chloro-2-hydroxy-propane;
3-(8-morpholino-3-ethyl-1-methyl-3,7-dihydro-1H-purine-2,6-dion-7-yl)-1-chloro-2-hydroxy-propane; and
3-(8-mropholino-3-methyl-1-n-propyl-3,7-dihydro-1H-purine-2,6-dion-7-yl)-1-chloro-2-2-hydroxy-propane.

Similarly, using the procedure of Paragraph A of this example, but substituting or 8-morpholino-theophylline, the compounds prepared in paragraph C of Preparation A, one obtains:

3-(8-benzylamino-1,3-dimethyl-3,7-dihydro-1H-purine-2,6-dion-7-yl)-1-chloro-2-hydroxy-propane;
3-(8-n-propylamino-1,3-dimethyl-3,7-dihydro-1H-purine-2,6-dion-7-yl)-1-chloro-2-hydroxy-propane; and
3-(8-diethylamino-1,3-dimethyl-3,7-dihydro-1H-purine-2,6-dion-7-yl)-1-chloro-2-hydroxy-propane.

PREPARATION C

Preparation of 7-(3-chloropropyl)-theophylline
(Compound of Formula IIa)

A well stirred reaction medium containing 1 mole theophylline, 3 moles 1-bromo-3-chloro-propane, 600 ml isopropyl alcohol and 60 ml water is refluxed for 24 hours.

An aqueous solution of potassium hydroxide (1.2 mole) is then slowly added dropwise thereto.

The alcohol solvent is then removed, the resulting material is extracted with methylene chloride, washed with water, after which the solvent is evaporated off, and the product, 7-(3-chloropropyl)-theophylline, is recrystallized from methanol, m.p. 122° C.

PREPARATION D

Preparation of 3-phenylthio-1-chloropropane
(Compound of formula IV)

To a solution containing 1.1 mole sodium hydroxide in 500 ml water are added 1 mole thiophenol and 2 moles 1-bromo-3-chloro-propane. The mixture is then refluxed for 30 hours, with vigorous stirring. After cooling, the resulting material is extracted with methylene chloride. After washing with dilute lye, and then with water, the solvent is evaporated in vacuo. The product, 3-phenylthio-1-chloropropane, distills at 138°–140° C. under 13 mm Hg.

PREPARATION E preparation of 1-(3-phenylthiopropyl)piperazine
(Compound of formula III)

To 1 liter 50% aqueous alcohol are added 3 moles piperazine, 1 mole 3-phenylthio-1-chloropropane, 1 mole 10N sodium hydroxide. The mixture is refluxed for 24 hours, with stirring. The methanol is then evaporated off, and the resulting material is extracted with methylene chloride. The organic phase is thoroughly washed with water, and is then concentrated and distilled, to give 1-(3-phenylthiopropyl)piperazine, bp$_{0.5}$ mm = 140°–142° C.

EXAMPLE 1

Preparation of
1-[3-(8-morpholino-3-i-butyl-1-methyl-3,7-dihydro-1H-purine-2,6-dion-7-yl)-2-hydroxypropyl]-4-(3-phenylthiopropyl)piperazine (Step c - Reaction Scheme 1)

0.5 moles of the 3-(8-morpholino-1-i-butyl-3-methyl-3,7-dihydro-1H-purine-2,6-dion-7-yl)-2-hydroxypropyl chloride prepared as in Preparation B and 0.5 moles of 1-(3-phenylthiopropyl)-piperazine, which was prepared in Preparation E, were dissolved in one liter of ethyl alcohol and refluxed for 5 hours. The solvent was partially removed, and the product precipitated out. The product was filtered off and recrystallized from ethanol to give the free base form of the title compound.

The dihydrochloride was prepared according to the procedure of Example 3 herein, melting point 216° C.

EXAMPLE 2

Preparation of
1-[3-(3-i-butyl-1-methyl-3,7-dihydro-1H-purine-2,6-dion-7-yl)-2-hydroxypropyl]-4-(3-phenylthiopropyl)-piperazine (Step e - Reaction Scheme 2)

0.5 moles of 1-[3-(3-i-butyl-1-methyl-3,7-dihydro-1H-purine-2,6-dion-7:yl)-2-hydroxypropyl]piperazine and 0.5 moles of 3-phenylthiopropyl chloride are dissolved in a liter of ethanol and refluxed for several hours. Upon evaporation of about half of the solvent, the product precipitates out, is filtered off, and is recrystallized from ethanol to give the free base form of 1-[3-(3-i-butyl-1-methyl-3,7-dihydro-1H-purine-2,6-dion-7-yl)-2-hydroxypropyl]-4-(3-phenylthiopropyl)piperazine.

The dihydrochloride derivative salt is prepared in the manner indicated in Example 3, m.p. 238° C.

EXAMPLE 3

Conversion of free base to salt

Excess 3% hydrogen chloride in methanol is added to a solution of 1.0 g. 1-[3-(3-i-butyl-1-methyl-3,7-dihydro-1H-purine-2,6-dion-7-yl)-2-hydroxypropyl]-4-(3-phenylthiopropyl)piperazine in 20 ml methanol. Diethyl ether is added until precipitation is complete. The product dihydrochloride is filtered, washed with ether, air dried and recrystallized, m.p. 238° C.

In a similar manner, all compounds of Formula I in free base form may be converted to the acid addition salts by treatment with the appropriate acid, for example, hydrochloric acid, hydrobromic acid, sulfuric acid, nitric acid, phosphoric acid, acetic acid, propionic acid, glycolic acid, pyruvic acid, oxalic acid, malonic acid, succinic acid, malic acid, maleic acid, fumaric acid, tartaric acid, citric acid, benzoic acid, cinnamic acid, mandelic acid, methanesulfonic acid, ethanesulfonic acid, p-toluenesulfonic acid, and the like.

EXAMPLE 4

Conversion of salt to free acid.

1.0 g of 1-[3-(3-i-butyl-1-methyl-3,7-dihydro-1H-purine-2,6-dion-7-yl)-2-hydroxypropyl]-4-(3-phenylthiopropyl)piperazine . 2HCl suspended in 50 ml of ether is stirred with excess dilute aqueous potassium carbonate solution until the salt is completely dissolved. The organic layer is then separated, washed twice with water, dried over magnesium sulfate and evaporated to yield 1-[3-(3-i-butyl-1-methyl-3,7-dihydro-1H-purine-2,6-dion-7-yl)-2-dihydroxypropyl]-4-(3-phenylthiopropyl)-piperazine as the free base.

EXAMPLE 5

Conversion of alcohol to ester.

(A) 1.0 grams of 1-[3-(3-i-butyl-1-methyl-3,7-dihydro-1H-purine-2,6-dion-7-yl)-2-hydroxypropyl]-4-(3-phenylthiopropyl)piperazine is dissolved in 30 ml pyridine. 2 ml of acetic anhydride is then added. The mixture kept at room temperature for 20 hours. Solvent is evaporated and the ester 1-[3-(3-i-butyl-1-methyl-3,7-dihydro-1H-purine-2,6-dion-7-yl)-2-acetoxypropyl]-4-(3-phenylthiopropyl)-piperazine is then isolated, recrystallized by conventional techniques, as the dihydrochloride.

(B) In a manner similar to that described in part A of this Example, the corresponding n-propionyloxy; i-butyryloxy; n-oxy, and n-caproyloxy valeryl compounds of derived from 1-[3-(3-i-butyl-1-methyl-3,7-dihydro-1H-purine-2,6-dion-7-yl)-2-hydroxypropyl]-4-(3-phenylthiopropyl)piperazine are prepared.

EXAMPLE 6

Following the procedures of Examples 1 to 5, compounds of Formula I may also be prepared as the free bases or as the salts. For example, the following have been so prepared:

(A) In the following, $R_1$ and $R_2$ are hydrogen, $R_4$ is methyl, m and n are both =1, and M is hydrogen.

| No. | $R_3$ | $R_5$ | $Z_1$ | $Z_2$ | Y | m.p. of dihydrochloride |
|---|---|---|---|---|---|---|
| (1) | H | i-propyl | CHOH | CHOH | S | 224° C. |
| (2) | H | i-propyl | CHOH | $CH_2$ | O | 242° C. |
| (3) | H | i-butyl | CHOH | $CH_2$ | O | 212° C. |
| (4) | H | i-butyl | CHOH | CHOH | S | 220° C. |
| (5) | 4-$CH_3$ | i-butyl | CHOH | $CH_2$ | S | 208° C. |
| (6) | H | i-propyl | CHOH | $CH_2$ | S | 214° C. |
| (7) | H | i-propyl | $CH_2$ | $CH_2$ | O | 246° C. |
| (8) | H | i-propyl | $CH_2$ | $CH_2$ | S | 204° C. |
| (9) | H | i-butyl | CHOH | $CH_2$ | S | 238° C. |
| (10) | 4-Cl | i-butyl | CHOH | $CH_2$ | O | 198° C. |
| (11) | H | n-propyl | CHOH | $CH_2$ | O | 215° C. |
| (12) | H | n-propyl | CHOH | CHOH | S | 196° C. |
| (13) | 4-$CH_3$ | n-propyl | CHOH | $CH_2$ | S | 174° C. |
| (14) | 4-$CH_3$ | i-propyl | CHOH | $CH_2$ | S | 212° C. |
| (15) | 4-$CH_3$ | n-butyl | CHOH | $CH_2$ | S | 186° C. |
| (16) | H | n-butyl | CHOH | CHOH | S | 194° C. |
| (17) | H | n-butyl | CHOH | CHOH | O | 218° C. |
| (18) | 4-Cl | n-butyl | CHOH | $CH_2$ | O | 216° C. |
| (19) | 4-Cl | n-butyl | CHOH | $CH_2$ | S | 202° C. |
| (20) | 4-Cl | i-butyl | CHOH | CHOH | S | 212° C. |
| (21) | 4-Cl | i-butyl | $CH_2$ | CHOH | S | 198° C. |
| (22) | 4-Cl | i-butyl | $CH_2$ | $CH_2$ | O | 224° C. |
| (23) | 4-Cl | i-butyl | CHOH | CHOH | O | 186° C. |
| (24) | 4-Cl | i-butyl | $CH_2$ | CHOH | O | 226° C. |

B. In the following, $R_1$ and $R_2$ are hydrogen, $R_4$ and $R_5$ are methyl, and m and n are both 1:

| No. | $R_3$ | $Z_1$ | $Z_2$ | Y | M | m.p. of dihydrochloride |
|---|---|---|---|---|---|---|
| (1) | H | CHOH | $CH_2$ | S | morpholino | 180° C. |
| (2) | 4-Cl | CHOH | $CH_2$ | O | morpholino | 190° C. |
| (3) | 4-$CH_3$ | CHOH | $CH_2$ | S | morpholino | 188° C. |
| (4) | 4-$CH_3$ | CHOH | $CH_2$ | S | di-n-butylamino | 144° C. |
| (5) | H | CHOH | CHOH | S | di-n-butylamino | 202° C. |
| (6) | 4-Cl | CHOH | $CH_2$ | O | di-n-butylamino | 160° C. |
| (7) | H | CHOH | $CH_2$ | S | benzylamino | 172° C. |
| (8) | H | CHOH | $CH_2$ | S | n-butylamino | 240° C. |

-continued

| No. | R₃ | Z₁ | Z₂ | Y | M | m.p. of dihydro-chloride |
|---|---|---|---|---|---|---|
| (9) | H | CHOH | CH₂ | O | n-butylamino | 235° C. |
| (10) | H | CHOH | CH₂ | S | 1-(2-methoxy-phenyl)-piperazin-4-yl | 186° C. |

C. The following have also been prepared:

1-[3-(8-n-butylamino-1,3-dimethyl-3,7-dihydro-1H-purine-2,6-dione-7-yl)-2-hydroxypropyl]-4-[3-(2,6-dimethylphenyl)oxypropyl]piperazine dihydrochloride, m.p. 220° C.;

1-[3-(8-morpholino-3-n-butyl-1-methyl-3,7-dihydro-1H-purine-2,6-dione-7-yl)-2-hydroxypropyl]-4-(3-phenyl)thiopropyl)piperazine dihydrochloride, m.p. 216° C.;

1-[3-(1,3-di-n-butyl-3,7-dihydro-1H-purine-2,6-dion-7-yl)propyl]-4-[3-(4-methylphenyl)thiopropyl]piperazine dihydrochloride, m.p. 208° C.

EXAMPLE 7

Pharmaceutical Compositions

The active ingredient in this example is 1-[3-(3-i-butyl-1-methyl-3,7-dihydro-1H-purine-2,6-dion-7-yl)-2-hydroxypropyl]-4-(3-phenylthiopropyl)piperazine. The other compounds of this invention may, of course, also be used.

| A. | CAPSULES | |
|---|---|---|
| | Active Ingredient | 30.0 mg |
| | Lactose, special | 163.0 mg |
| | Talc | 5.0 mg |
| | Magnesium stearate | 2.0 mg |
| B. | INJECTABLE AMPOULES | |
| | Active Ingredient | 10.0 mg |
| | Sodium chloride | 35.0 mg |
| | Monosodium phosphate, to pH 5.5–6 | |
| | Distilled water, qs ad | 5.0 ml |
| C. | TABLETS | |
| | Active Ingredient | 10.0 mg |
| | Lactose | 80.0 mg |
| | Cellulose | 97.5 mg |
| | Silica | 1.5 mg |
| | Starch | 10.0 mg |
| | Magnesium stearate | 1.0 mg |
| D. | DRINKABLE SUSPENSION | |
| | Active Ingredient | 200.0 mg |
| | Benzoic acid | 250.0 mg |
| | Polyoxyethylene glycol and water, qs ad | 200.0 ml |
| E. | AEROSOL I | |
| | Active Ingredient | 0.6% |
| | Span 85 | 0.5% |
| | Freon 11 | 20.0% |
| | Freon 12/Freon 114 (20/80) | 78.9% |
| | AEROSOL II | |
| | Active Ingredient | 0.88% |
| | Sodium sulfate (anhydrous), micronized | 0.88% |
| | Span 85 | 1.00% |
| | Propellant consisting of 50% Freon 12, 25% Freon 11, and 25% Freon 114 | 97.24% |
| | AEROSOL III | |
| | Active Ingredient | 0.50% |
| | Span 80 | 0.50% |
| | Propellant (C) consisting of 30% Freon 11 and 70% Freon W | 99.0% |
| | AEROSOL IV | |
| | Active Ingredient | 3.0% |
| | Span 85 (sorbitan trioleate) | 1.0% |
| | Freon 11 (trichloromonofluoromethane) | 30.0% |
| | Freon 114 (dichlorotetrafluoroethane) | 41.0% |

-continued

| | |
|---|---|
| Freon 12 (dichlorodifluoromethane) | 25.0% |

What is claimed is:

1. A compound of the formula

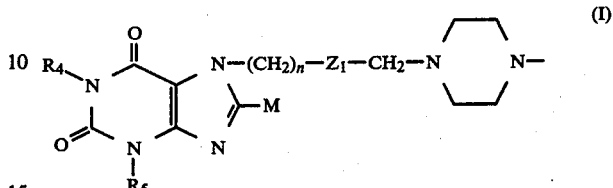

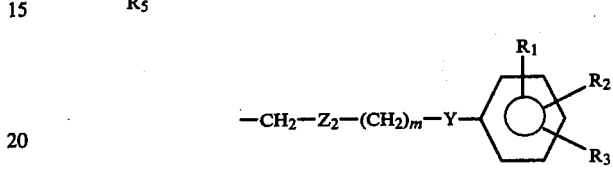

and the pharmaceutically acceptable acid addition salts thereof, wherein

M is selected from the group consisting of hydrogen, morpholino, benzylamino, di-n-lower alkylamino, n-lower alkylamino, and

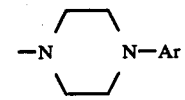

wherein Ar is optionally substituted phenyl;

$Z_1$ and $Z_2$ are each independently selected from the group consisting of $CH_2$, CHOB and C=O, wherein B is selected from the group consisting of hydrogen and alkanoyl;

Y is oxygen or sulfur;

n is an integer from 0–4 but cannot be zero when $Z_1$ is CHOB;

m is an integer from 0–4 but cannot be zero when $Z_2$ is CHOB, or when M is hydrogen;

$R_1$, $R_2$ and $R_3$ are each independently hydrogen, halogen, hydroxy, trifluoromethyl, alkyl or alkoxy; and $R_4$ and $R_5$ are each independently lower alkyl, with the proviso that both $R_4$ and $R_5$ cannot be methyl when M is hydrogen.

2. The compound of claim 1 and the pharmaceutically acceptable acid addition salts thereof wherein $Z_1$ and $Z_2$ are each independently $CH_2$ or CHOH; m and n are both 1; and at least one of $R_1$, $R_2$ and $R_3$ is hydrogen.

3. The compound of claim 2 and the pharmaceutically acceptable acid addition salts thereof wherein either at least one of $R_4$ and $R_5$ is methyl, or both $R_4$ and $R_5$ are identical; and either at least two of $R_1$, $R_2$ and $R_3$ are hydrogen or two of these are otherwise identical.

4. The compound of claim 3 and the pharmaceutically acceptable acid addition salts thereof which is 1-[3-(3-i-butyl-1-methyl-3,7-dihydro-1H-purine-2,6-dion-7-yl)-2-hydroxypropyl]-4-(3-phenylthiopropyl)-piperazine.

5. The compound of claim 3 and the pharmaceutically acceptable acid addition salts thereof which is 1-(3-(8-morpholino-3-i-butyl-1-methyl-3,7-dihydro-1H-purine-2,6-dion-7-yl)-2-hydroxypropyl]-4-(3-phenylthiopropyl)piperazine.

6. The compound of claim 3 and the pharmaceutically acceptable acid addition salts thereof which is 1-[3-(3-i-butyl-1-methyl-3,7-dihydro-1H-purine-2,6-dion-7-yl)-2-hydroxypropyl]-4-(3-phenoxypropyl)piperazine.

7. The compound of claim 3 and the pharmaceutically acceptable acid addition salts thereof which is 1-[3-(3-i-butyl-1-methyl-3,7-dihydro-1H-purine-2,6-dion-7-yl)-2-hydroxypropyl]-4-(3-phenylthio-2-hydroxypropyl)piperazine.

8. The compound of claim 3 and the pharmaceutically acceptable acid addition salts thereof which is 1-[3-(3-i-butyl-1-methyl-3,7-dihydro-1H-purine-2,6-dion-7-yl)-2-hydroxypropyl]-4-[3-(4-methylphenylthio)-propyl]piperazine.

9. The compound of claim 3 and the pharmaceutically acceptable acid addition salts thereof which is 1-[3-(3-n-butyl-1-methyl-3,7-dihydro-1H-purine-2,6-dion-7-yl)-2-hydroxypropyl]-4-(3-phenylthiopropyl)-piperazine.

10. The compound of claim 3 and the pharmaceutically acceptable acid addition salts thereof which is 1-[3-(3-i-butyl-1-methyl-3,7-dihydro-1H-purine-2,6-dion-7-yl)propyl]-4-(3-phenoxypropyl)piperazine.

11. The compounds of claim 3 and the pharmaceutically acceptable acid addition salts thereof which is 1-[3-(8-morpholino-1,3-dimethyl-3,7-dihydro-1H-purine-2,6-dion-7-yl)-2-hydroxypropyl]-4-(3-phenylthiopropyl)piperazine.

12. The compound of claim 3 and the pharmaceutically acceptable acid addition salts thereof which is 1-[3-(8-morpholino-1,3-dimethyl-3,7-dihydro-1H-purine-2,6-dion-7-yl)-2-hydroxypropyl]-4-[3-(4-methylphenylthiopropyl]piperazine;

13. The compound of claim 3 and the pharmaceutically acceptable acid addition salts thereof which is 1-[3-(8-n-butylamino-1,3-dimethyl-3,7-dihydro-1H-purine-2,6-dion-7-yl)-2-hydroxypropyl]-4-[3-(2,6-dimethylphenoxy)-propyl]piperazine.

14. The compound of claim 3 and the pharmaceutically acceptable acid addition salts thereof which is 1-[3-(8-morpholino-3-n-butyl-1-methyl-3,7-dihydro-1H-purine-2,6-dion-7-yl)-2-hydroxypropyl]-4-(3-phenylthiopropyl)piperazine.

15. A pharmaceutical composition for treating respiratory diseases or effecting vasodilation in mammals, which comprises a therapeutically effective amount of the compound of claim 1 or a pharmaceutically acceptable acid addition salt thereof, in admixture with at least one pharmaceutically acceptable, non-toxic excipient.

16. A method for treating respiratory diseases in mammals, which method comprises administering to a subject in need of such treatment, an effective amount of, or a pharmaceutical composition containing an effective amount of a compound of claim 1 or a pharmaceutically acceptable acid addition salt thereof.

17. A method for effecting vasodilation in human beings which method comprises administering to a subject in need of such treatment a therapeutically effective amount of, or a pharmaceutical composition containing a therapeutically effective amount of, the compound of claim 1 or a pharmaceutically acceptable acid addition salt thereof.

* * * * *